(12) United States Patent
Boaz

(10) Patent No.: US 6,620,954 B1
(45) Date of Patent: Sep. 16, 2003

(54) PHOSPHINOMETALLOCENYLAMIDES AS NOVEL LIGANDS FOR ASYMMETRIC CATALYSIS

(75) Inventor: Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 8 days.

(21) Appl. No.: 10/105,516

(22) Filed: Mar. 25, 2002

(51) Int. Cl.$^7$ .................. C07F 17/00; B01J 31/00; C07C 69/34
(52) U.S. Cl. .................. 556/16; 556/145; 556/28; 502/155; 562/480; 560/127; 560/190
(58) Field of Search .................. 556/16, 145; 502/155; 560/127, 190; 562/480

(56) References Cited

U.S. PATENT DOCUMENTS

| | | | | |
|---|---|---|---|---|
| 5,041,582 A | * | 8/1991 | Eida et al. | 556/143 |
| 5,856,540 A | * | 1/1999 | Jendralla | 556/21 |
| 6,015,919 A | * | 1/2000 | Pugin | 556/145 |
| 6,133,464 A | * | 10/2000 | Pugin et al. | 556/14 |

FOREIGN PATENT DOCUMENTS

| | | | |
|---|---|---|---|
| DE | 199 18 420 | | 10/2000 |
| WO | WO 98/01457 | * | 1/1998 |

OTHER PUBLICATIONS

Richards et al, Tetrahedron: Asymmetry 9, 1998, pp. 2377–2407.
Clayden et al, J. Org. Chem., 2000, vol. 65, pp. 7033–7040.
Mino et al, Tetrahedron: Asymmetry 12, 2001, pp. 287–291.
Trost et al, Tetrahedron Letters, 1994, vol. 35, No. 32, pp. 5817–5820.
Butts et al, J. Chem. Soc. Chem. Commun., 1999, pp. 1707–1708.
Kim et al, J. Org. Chem., 2000, vol. 65, pp. 7807–7813.
Marquarding et al, J. Am. Chem. Soc., 1970, vol. 92, pp. 5389–5393.
Armstrong et al, Anal. Chem., 1985, vol. 57, No. 2, pp. 481–484.
Boaz et al, Tetrahedron Letters, 1989, vol. 30, No. 16, pp. 2061–2064.
Hayashi et al, Bull. Chem. Soc. Japan, 1980, vol. 53, No. 4, pp. 1138–1151.

* cited by examiner

*Primary Examiner*—Porfirio Nazario-Gonzalez
(74) *Attorney, Agent, or Firm*—Michael J. Blake; Bernard J. Graves, Jr.

(57) ABSTRACT

Disclosed are novel phosphinometallocenylamides that are useful as ligands for asymmetric catalysis. The novel ligands, which are readily modifiable, contain both a phosphine and an amide functionality linked by a metallocene backbone. In addition, the novel compounds are phosphine-amides derived from a phosphine-amine, rather than a phosphine-carboxylic acid. Further, described herein are both processes to make the novel ligands as well as processes that employ such ligands in a catalytically active composition comprising one or more phosphinometallocenylamide compounds in complex association with one or more Group VIb or Group VIII metals to provide chiral products. Further, we describe exemplary catalyst complexes incorporating the novel ligands.

26 Claims, No Drawings

PHOSPHINOMETALLOCENYLAMIDES AS NOVEL LIGANDS FOR ASYMMETRIC CATALYSIS

FIELD OF THE INVENTION

The present invention relates to novel ligands for asymmetric catalysis, as well as methods for making and using the novel compounds. The novel ligands, which are readily modifiable, contain both a phosphine and an amide functionality linked by a metallocene backbone. In addition, the novel compounds are phosphine-amides derived from a phosphine-amine, rather than a phosphine-carboxylic acid. The invention further relates to employing the resulting substantially enantiomerically pure ligands in a catalytically active composition comprising one or more phosphinometallocenylamide compounds in complex association with one or more Group VIb or Group VIII metals.

BACKGROUND OF THE INVENTION

Asymmetric catalysis is the most efficient method for generating products with high enantiomeric purity, since the asymmetry of the catalyst is multiplied many times over in generating the chiral product. Such chiral products have found numerous applications as building blocks in, for example, single enantiomer pharmaceuticals and agrochemicals.

Asymmetric catalysts used to make such chiral products can be enzymatic or synthetic in nature. The synthetic catalysts have much greater promise than the enzymatic catalysts because of a much greater latitude in the types of reactions in which they may be used. Synthetic asymmetric catalysts usually contain a metal reaction center surrounded by an organic ligand. The ligand used is ordinarily of high enantiomeric purity, and is the agent inducing the asymmetry to the reaction product. Such ligands are, in general, difficult to make and therefore expensive.

As described by Richards, C. J. et al., *Tetrahedron: Asymmetry* 1998, 9, 2377–2407, asymmetric ferrocene derivatives have found great utility as ligands for asymmetric catalysis in reactions as varied as asymmetric hydrogenations, asymmetric Aldol reactions, asymmetric organometallic additions, and asymmetric hydrosilations. These ferrocene species usually are bidentate in nature, using a variety of ligating species. There are, however, no reported cases of metallocenyl ligands possessing one phosphine and one amide as the sole ligating groups.

Mixed phosphine-amides have recently been reported as ligands for asymmetric allylation reactions. See, Clayden, J. et al., *J. Org. Chem.* 2000, 65, 7033–7040; and Mino, T. et al., *Tetrahedron:Asymmetry* 2001, 12, 287–291. In addition, there have been reports of multi-dentate ligands that may, under certain conditions, function as phosphine-amide ligands, Trost, B. M. et al., *Tetrahedron Lett.* 1994, 35, 5817–5820; Butts, C. P. et al., *J. Chem. Soc. Chem. Commun.* 1999, 1707–1708; and Kim, Y. K. et al., *J. Org. Chem.* 2000, 65, 7807–7813. All of the ligands described in the foregoing have generally afforded only moderate enantioselectivities, and in no cases gave results above 90% ee (enantomeric excess). In addition, all of the previous phosphine-amide ligands are based on a 2-diphenylphosphinobenzoic acid amide; there are no cases of phosphine-amide ligands based on an amide of a phosphine-amine substructure, and none uses a metallocene backbone.

There continues to exist a need for stable, substantially enantiomerically pure ligands that enable one to make chiral products with which to create a variety of useful chemicals, such as pharmaceuticals and agrochemicals.

BRIEF SUMMARY OF THE INVENTION

I have prepared novel, substantially enantiomerically pure phosphinometallocenylamides having the general structures below

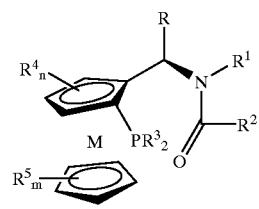

1

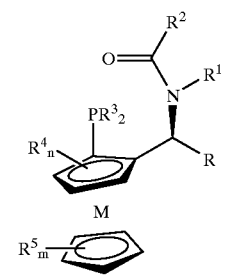

2 as bidentate ligands for asymmetric catalysis. The ligands are particularly useful in, for example, asymmetric allylation reactions, affording products with high enantiomeric excess.

In addition, described more fully below are both processes to make the novel bidentate ligands as well as processes that employ such ligands. Further, exemplary catalyst complexes incorporating the novel ligands are described.

DETAILED DESCRIPTION

I have discovered a series of novel, substantially enantiomerically pure phosphine-amides having an amide derived from a chiral phosphinometallocenylamine. Examples of the substantially enantiomerically pure, compounds include phosphinometallocenylamides having the general formulas 1 and 2 (the enantiomer of 1):

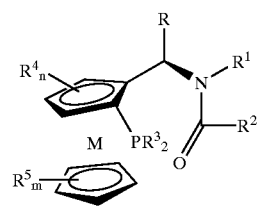

1

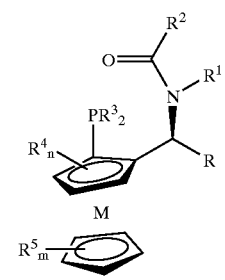

2 wherein
R is selected from substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl having up to three heteroatoms selected from sulfur, nitrogen, and oxygen;

$R^1$, $R^2$, $R^3$, $R^4$, and $R^5$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

n is 0 to 3;

m is 0 to 5; and

M is selected from the metals of Groups IVB, VB, VIB, VIIB and VIII.

As used herein, the phrase "substantially enantiomerically pure" refers to an enantiomeric excess (ee) of 90% or greater.

The alkyl groups that may be represented by each of R, $R^1$, $R^2$, $R^3$, $R^4$, and $R^5$ may be straight- or branched-chain, aliphatic hydrocarbon radicals containing up to about 20 carbon atoms and may be substituted, for example, with one to three groups selected from $C_1$–$C_6$-alkoxy, cyano, $C_2$–$C_6$-alkoxycarbonyl, $C_2$–$C_6$-alkanoyloxy, formyloxy, hydroxy, aryl and halogen. The terms "$C_1$–$C_6$-alkoxy", "$C_2$–$C_6$-alkoxycarbonyl", and "$C_2$–$C_6$-alkanoyloxy" are used to denote radicals corresponding to the structures —$OR^6$, —$CO_2 R^6$, and —$OCOR^6$, respectively, wherein $R^6$ is $C_1$–$C_6$-alkyl or substituted $C_1$–$C_6$-alkyl. The term "$C_3$–$C_8$-cycloalkyl" is used to denote a saturated, carbocyclic hydrocarbon radical having three to eight carbon atoms and may be substituted, for example, with one to three groups selected from $C_1$–$C_6$-alkoxy, cyano, $C_2$–$C_6$-alkoxycarbonyl, $C_2$–$C_6$-alkanoyloxy, formyloxy, hydroxy, aryl and halogen. The aryl groups that each of R, $R^1$, $R^2$, $R^3$, $R^4$, and $R^5$ may represent may include phenyl, naphthyl, or anthracenyl and phenyl, naphthyl, or anthracenyl substituted with one to three substituents selected from $C_1$–$C_6$-alkyl, substituted $C_1$–$C_6$-alkyl, $C_6$–$C_{10}$ aryl, substituted $C_6$–$C_{10}$ aryl, $C_1$–$C_6$-alkoxy, halogen, carboxy, cyano, $C_1$–$C_6$-alkanoyloxy, $C_1$–$C_6$-alkylthio, $C_1$–$C_6$-alkylsulfonyl, trifluoromethyl, hydroxy, $C_2$–$C_6$-alkoxycarbonyl, $C_2$–$C_6$-alkanoylamino and —O—$R^7$, —S—$R^7$, —$SO_2$—$R^7$, —$NHSO_2R^7$ and —$NHCO_2R^7$, wherein $R^7$ is phenyl, naphthyl, or phenyl or naphthyl substituted with one to three groups selected from $C_1$–$C_6$-alkyl, $C_6$–$C_{10}$ aryl, $C_1$–$C_6$-alkoxy and halogen.

The heteroaryl radicals include a 5- or 6-membered aromatic ring containing one to three heteroatoms selected from oxygen, sulfur and nitrogen. Examples of such heteroaryl groups are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heteroaryl radicals may be substituted, for example, with up to three groups such as $C_1$–$C_6$-alkyl, $C_1$–$C_6$-alkoxy, substituted $C_1$–$C_6$-alkyl, halogen, $C_1$–$C_6$-alkylthio, aryl, arylthio, aryloxy, $C_2$–$C_6$-alkoxycarbonyl and $C_2$–$C_6$-alkanoylamino. The heteroaryl radicals also may be substituted with a fused ring system, e.g., a benzo or naphtho residue, which may itself be unsubstituted or substituted, for example, with up to three of the groups set forth in the preceding sentence.

The term "halogen" is used to include fluorine, chlorine, bromine, and iodine. It is also understood that the $R^4$ or $R^5$ groups are meant, when present, to replace a hydrogen on the aromatic ring and not to create a saturated carbon.

The compounds of the invention which presently are preferred have formulas 1 or 2 wherein R is $C_1$ to $C_6$ alkyl; $R^1$ is hydrogen or $C_1$ to $C_6$ alkyl; $R^2$ is $C_1$ to $C_6$ alkyl or phenyl; $R^3$ is aryl, most preferably phenyl; $R^4$ and $R^5$ are hydrogen (i.e., m=n=0); and M is iron, ruthenium, or osmium. The compounds of the invention which presently are most preferred have formulas 1 or 2 wherein R is methyl, $R^1$ is hydrogen, $R^2$ is methyl, ethyl, or phenyl, $R^4$ and $R^5$ are hydrogen (i.e., n=m=0), and M is iron.

The compounds of my invention contain both a phosphine and an amide functionality linked by a metallocene backbone. In addition, the compounds of my invention are phosphine-amides that are derived from a phosphine-amine rather than a phosphine-carboxylic acid. Further, the metallocene-based ligands are readily modifiable. For example, as shown below in constructing the novel ligands, one may vary $R^1$ according to the choice of the amine used (see, Step (2), below), and $R^2$ according to the carboxylic acid piece used (see, Step (3), below), which thus allows simple modification of the reactivity and selectivity of the catalyst prepared from these ligands.

My invention also provides novel processes for preparing compounds of formulas 1 and 2. Thus, an embodiment of the present invention involves a process for preparing a substantially enantiomerically pure compound having formula 1:

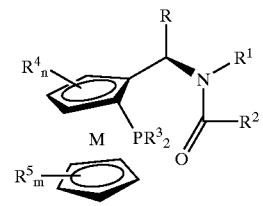

1 which comprises the steps of:

(1) contacting an amine having formula 3:

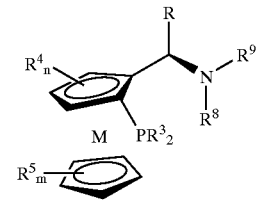

3 with a carboxylic acid anhydride having the formula $(R^{10}CO)_2O$ to obtain an ester compound having formula 4:

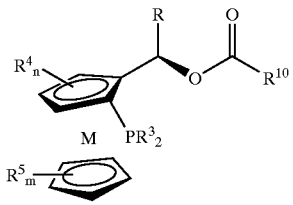

4

(2) contacting the ester 4 with an amine having the formula H$_2$N—R$^1$ to obtain an intermediate aminophosphine compound having formula 5:

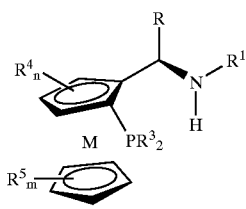

5

(3) contacting intermediate compound 5 with an acid anhydride or acid chloride of formula (R$^2$CO)$_2$O or R$^2$COX;

wherein R, R$^1$, R$^2$, R$^3$, R$^4$, R$^5$, n, m, and M are as defined above, R$^8$ and R$^9$ are independently selected from substituted and unsubstituted, branched- and straight-chain C$_1$–C$_{20}$ alkyl, substituted and unsubstituted C$_3$–C$_8$ cycloalkyl, substituted and unsubstituted C$_6$–C$_{20}$ carbocyclic aryl, and substituted and unsubstituted C$_4$–C$_{20}$ heteroaryl wherein the heteroatoms are selected from sulfur, nitrogen, and oxygen, R$^{10}$ is a C$_1$ to C$_4$ alkyl radical, and X is chlorine, bromine, or iodine.

Likewise, compounds of formula 2 may be prepared when an amine having formula 6:

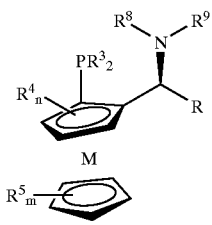

6 is used as the starting material affording intermediates 7 and 8 analogous to 4 and 5, respectively.

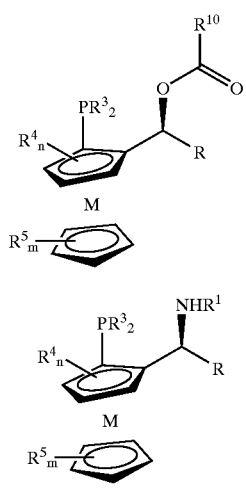

7

8

In the first step of the process to make 1, an amine reactant compound 3 is contacted with a carboxylic acid anhydride, (R$^{10}$CO)$_2$O, where R$^{10}$ is defined as above. The amount of anhydride used may be about 1 to 100 moles, preferably about 2 to 10 moles, per mole of amine reactant 3. Although the carboxylic anhydride may contain up to about 8 total carbon atoms, acetic anhydride is particularly preferred. The first step of the process may be carried out at a temperature between about 20° C. and the boiling point of the anhydride, preferably about 80 to 120° C. While an inert solvent may be used in step (1), such a solvent is not essential and the carboxylic acid anhydride may function as both solvent and reactant. At the completion of the first step, the ester intermediate may be isolated for use in the second step by conventional procedures such as crystallization, extractive purification, or removing the carboxylic anhydride and any extraneous solvents and co-products present, e.g., by distillation.

Amine reactant 3 may be prepared in high enantiomeric purity by several known methods. For example, precursor 9 having the following formula, in which "M" is represented as Fe:

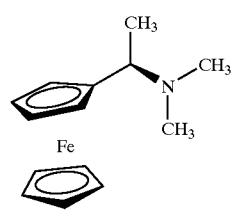

9 can be prepared in high enantiomeric purity using the procedures described by Marquarding, D. et al., *J. Am. Chem. Soc.* 1970, 92, 5389–5393; Armstrong, D. W. et al., *Anal. Chem.* 1985, 57, 481–484; and Boaz, N. W., *Tetrahedron Letters* 1989, 30, 2061–2064. Precursor 9 may then be converted by known procedures to amine reactant 3, e.g., using the procedures described in Hayashi, T. et al., *Bull Chem. Soc. Jpn.* 1980, 53, 1130–1151; and the references mentioned in the preceding sentence. The enantiomeric species 6, used to prepare 2, can be prepared in a like manner.

In the second step of the process, the ester intermediate 4 obtained from step (1) is contacted and reacted with an amine having the formula H$_2$NR$^1$ in the presence of a C$_1$ to C$_4$ alkanol solvent, preferably methanol or 2-propanol to provide 5. The second step may be carried out at a temperature between 20° C. and the boiling point of the solvent, preferably about 25 to 50° C. The mole ratio of the amine:ester intermediate 4 (or 7) typically is in the range of about 1:1 to 25:1. Intermediate 5 (or 8) may be recovered for use in step (3) by conventional procedures such as extractive purification or crystallization.

In the third step of my novel process, intermediate 5 (or 8) is contacted and reacted with a carboxylic acid derivative having the formula (R$^2$CO)$_2$O or R$^2$COX, wherein R$^2$ is as defined above. Further, when R$^2$COX is the carboxylic acid derivative employed in step (3), X is a halide chosen from chlorine, bromine, or iodine, a sulfonate such as methanesulfonate, trifluoromethanesulfonate, or p-toluenesulfonate and the like, an imidazole, or H wherein in the latter case the reaction is conducted using a coupling agent such as a carbodiimide or a 2-halo-1-methylpyridinium salt. The carboxylic acid derivative is preferably an acid anhydride or an acid halide. The reaction is conducted using a carboxylic acid derivative to intermediate 5 (or 8) mole ratio in the range of about 0.8:1 to 1.3:1.

The reaction of step (3) is preferably carried out in the presence of an acid acceptor such as a tertiary amine, e.g., trialkylamines containing a total of 3 to 15 carbon atoms, pyridine, substituted pyridines and the like. The amount of acid acceptor used normally is at least 1 mole of acid acceptor per mole of carboxylic acid derivative employed and up to 5 moles of acid acceptor per mole of carboxylic acid derivative.

Step (3) may be carried out in the presence of an inert solvent. Examples of inert solvents that may be used in step (3), or in step (1), include, but are not limited to, non-polar, aprotic solvents such as aliphatic and aromatic hydrocarbons containing 6 to 10 carbon atoms, e.g., hexane, heptane, octane, toluene, the various xylene isomers and mixtures thereof, and the like; halogenated, e.g., chlorinated, hydrocarbons containing up to about 6 carbon atoms such as dichloromethane, chloroform, tetrachloroethylene, chlorobenzene and the like; and cyclic and acyclic ethers containing from about 4 to 8 carbon atoms, e.g., tert-butyl methyl ether, diisopropyl ether, tetrahydrofuran and the like. The acid acceptor and solvent particularly preferred are triethylamine and toluene, respectively. Step (3) may be carried out at a temperature between about −20° C. and the boiling point of the solvent, preferably about 0 to 30° C.

The scope of the present invention includes employing the resulting substantially enantiomerically pure compounds as catalytically active compositions comprising one or more phosphinometallocenylamide compounds in complex association with one or more Group VIb or Group VIII metals, preferably palladium, platinum or molybdenum.

EXAMPLES

The novel compounds and processes provided by the present invention are further illustrated by the following examples. As used in the Examples, reference to my novel compounds and various intermediates is denoted by a number corresponding to the molecule in question followed by a lower case letter. In each case, the various moieties (e.g., R, $R^1$, $R^2$, etc.) are as indicated by the particular example.

Example 1

Preparation of (R)-1-[(S)-2-(Diphenylphosphino) ferrocenyl]ethylamine (R,S-5a)($R^1$=H)

(R)—N,N-Dimethyl-1-[(S)-2-(diphenylphosphino) ferrocenyl]ethylamine (R,S-3a, R=$R^8$=$R^9$=methyl, $R^3$=phenyl—Ph, $R^4$=$R^5$=H (i.e., n=m=0), M=Fe)(10.0 g; 22.7 mmol) was combined with acetic anhydride (14.25 mL; 150 mmol; 6.7 equivalents) in a 250-mL flask. The flask was evacuated and filled with nitrogen ten times and then heated to 100° C. for 2 hours, at which point thin layer chromatography (tlc) analysis indicated no 3a present. The residual acetic anhydride was evaporated at reduced pressure to afford a solid mass containing acetate ester R,S-4a. A portion (1.0 g) of acetate ester R,S-4a was removed and the remainder was dissolved in isopropanol (200 mL) and treated with concentrated ammonium hydroxide (28% $NH_3$; 24.3 mL; 360 mmol; 17.5 equiv). The reaction mixture was heated to 50° C. overnight to completely consume 4 according to tlc analysis. The mixture was concentrated to small volume at reduced pressure. The residue was dissolved in ethyl acetate and extracted with 10% aqueous citric acid (3×75 mL). The acidic extracts were neutralized with 4 N NaOH (115 mL) to pH 12 and extracted with ethyl acetate (3×50 mL). The combined organic solution was dried with magnesium sulfate and concentrated in vacuo to afford 7.34 g (87% yield) of R,S-5a ($R^1$=hydrogen). S,R-8a was prepared in the same manner from S,R-6a.

$^1$H NMR (CDCl$_3$) δ 7.6–7.2 (m, 10H); 4.43 (br s, 1H); 4.28 (m, 1H); 4.20 (m, 1H); 4.016 (s, 5H); 3.76 (m, 1H); 1.439 (d, 3H, J=6.59 Hz).

Example 2

Preparation of (R)-1-[(S)-2-(Diphenylphosphino) ferrocenyl]Ethyl Acetamide (R,S-1a)($R^1$=H, $R^2$=Me)

Amine R,S-5a (400 mg; 0.97 mmol) was dissolved in toluene (5 mL). The reaction mixture was placed in ice-water and purged with an argon stream for ten minutes. Triethylamine (0.20 mL; 1.45 mmol; 1.5 equiv) was added followed by acetic anhydride (110 μL; 1.16 mmol; 1.2 equiv). The reaction mixture was allowed to warm to ambient temperature and stirred overnight to afford complete consumption of 5a according to tlc analysis (2:1 ethyl acetate:heptane elution). The reaction mixture was diluted with water (5 mL) and heptane (5 mL) and stirred for five minutes. The precipitate was collected, washed with water and heptane, and air-dried to afford 0.27 g (61%) of R,S-1a.

$^1$H NMR (CDCl$_3$) δ 7.5 (m, 2H); 7.4 (m, 3H); 7.2 (m, 5H); 5.63 (m, 1H); 5.184 (m(5), 1H, J=7.14 Hz); 4.462 (s, 1H); 4.292 (m, 1H); 4.034 (s, 5H); 3.774 (s, 1H); 1.399 (d, 3H, J=6.59 Hz); 1.356 (s, 3H). FDMS: m/z 455.3 ($M^+$). $[\alpha]_D^{23}$−312° (c 1.00, methanol).

Example 3

Preparation of (R)-1-[(S)-2-(Diphenylphosphino) ferrocenyl]ethyl Propionamide (R,S-1b) ($R^1$=H $R^2$=Et)

Amine R,S-5a (480 mg; 1.16 mmol) was dissolved in toluene (5 mL). The reaction mixture was placed in ice-water and purged with an argon stream for 15 minutes. Triethylamine (0.24 mL; 1.74 mmol; 1.5 equiv) was added followed by propionic anhydride (178 μL; 1.39 mmol; 1.2 equiv). The reaction mixture was allowed to warm to ambient temperature over two hours to afford complete consumption of 5a according to tlc analysis (2:1 ethyl acetate:heptane elution). The reaction mixture was diluted with water (5 mL) and heptane (10 mL) and stirred for ten minutes. The precipitate was collected, washed with water and heptane, and air-dried to afford 0.40 g (73%) of R,S-1b.

$^1$H NMR (CDCl$_3$) δ 7.52 (m, 2H); 7.38 (m, 3H); 7.3–7.15 (m, 5H); 5.89 (m, 1H); 5.178 (m(5), 1H, J=6.87 Hz); 4.462 (s, 1H); 4.296 (m, 1H); 4.015 (s, 5H); 3.787 (m, 1H); 1.8–1.5 (m, 2H); 1.371 (d, 3H, J=6.87 Hz); 0.903 (t, 3H, J=7.69 Hz). FDMS: m/z 469.2 ($M^+$). $[\alpha]_D^{23}$−308° (c 1.05, methanol).

Example 4

Preparation of (R)-1-[(S)-2-(Diphenylphosphino) ferrocenyl]ethyl Benzamide (R,S-1c)($R^1$=H $R^2$=Ph)

Amine R,S-5a (400 mg; 0.97 mmol) was dissolved in toluene (5 mL). The reaction mixture was placed in ice-water and purged with an argon stream for 15 minutes. Triethylamine (0.20 mL; 1.45 mmol; 1.5 equiv) was added followed by benzoyl chloride (135 μL; 1.39 mmol; 1.2 equiv). The reaction mixture was allowed to warm to ambient temperature and stirred overnight to afford complete consumption of 5a according to tlc analysis (2:1 ethyl acetate:heptane elution). The reaction mixture was diluted with ethyl acetate, washed with 1 N HCl (15 mL) and saturated sodium bicarbonate (5 mL), dried with magnesium sulfate, and concentrated to afford 0.58 g (99%) of R,S-1c.

$^1$H NMR (CDCl$_3$) δ 7.7–7.1 (m, 15H); 5.342 (m(5), 1H, J=6.59 Hz); 4.611 (br s, 1H); 4.39 (m, 1H); 4.003 (s, 5H); 3.91 (m, 1H); 1.469 (d, 3H, J=6.59 Hz). FDMS: m/z 517.2 ($M^+$). $[\alpha]_D^{23}$−356° (c 1.10, methanol).

The use of compounds 1 or 2 requires that the ligand be complexed with a catalytically active metal ("metal"); that is, a metal other than the structural metal of the metallocene. The particular catalytically active metal chosen depends on the desired reaction. There are a large number of possible reactions of a wide variety of substrates using catalysts based on compounds 1 and 2, including but not limited to asymmetric hydrogenations, asymmetric reductions, asymmetric hydroborations, asymmetric olefin isomerizations, asymmetric hydrosilations, asymmetric allylations, and asymmetric organometallic additions. The utility of ligands 1 and 2 will be demonstrated herein through asymmetric allylation reactions of their metal complexes, which is also an embodiment of my invention. Thus, the present invention includes a process for the asymmetric allylation of a suitable allylic compound which comprises contacting the allylic electrophile compound with a nucleophile in the presence of a catalyst complex comprising ligands 1 or 2 in complex association with a metal.

The preferred allylic electrophile reactants have the general formula 10,

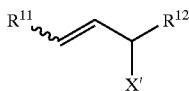

10 wherein $R^{11}$ and $R^{12}$ are independently selected from hydrogen, substituted and unsubstituted, branched- and straight-chain $C_1$ to $C_{20}$ alkyl, substituted and unsubstituted $C_3$ to $C_8$ cycloalkyl, substituted and unsubstituted $C_6$ to $C_{20}$ carbocyclic aryl, and substituted and unsubstituted $C_4$ to $C_{20}$ heteroaryl wherein the heteroatoms are selected from sulfur, nitrogen, or oxygen; or $R^{11}$ and $R^{12}$ collectively represent a substituted or unsubstituted alkylene group of 0–5 chain carbon atoms; and X' is chosen from chloride, bromide, iodide, sulfonates of formula —OSO2R$^{13}$, esters of formula —OCOR$^{13}$, and carbonates of formula —OCOOR$^{13}$, wherein R$^{13}$ is selected from hydrogen, substituted and unsubstituted, branched- and straight-chain $C_1$ to $C_{20}$ alkyl, substituted and unsubstituted $C_3$ to $C_8$ cycloalkyl, substituted and unsubstituted $C_6$ to $C_{20}$ carbocyclic aryl, and substituted and unsubstituted $C_4$ to $C_{20}$ heteroaryl wherein the heteroatoms are selected from sulfur, nitrogen, or oxygen.

The nucleophiles mentioned above (that are reacted with allylic electrophiles) are of the form Nu—H. These nucleophiles include species such as soft carbon acids such as malonates, 3-ketoesters, 2-cyanoesters, and the like, substituted or unsubstituted $C_1$–$C_{20}$ alcohols, substituted or unsubstituted phenols, and substituted or unsubstituted $C_1$–$C_{20}$ amines.

The products of the allylation reactions of the allylic electrophiles having formula 10 with catalysts based on ligands 1 and 2 are comprised of species with formula 11 or 12,

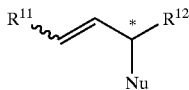

11

-continued

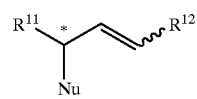

12 wherein $R^{11}$ and $R^{12}$ are as defined above. These compounds are generally produced with high enantioselectivity (>80% ee), with the particular enantiomer produced depending upon whether ligand 1 or ligand 2 is used.

For an asymmetric allylation reaction, the metal complexed can be chosen from the group consisting of palladium, platinum, or molybdenum, and is most preferably palladium. The ligand-metal complex can be prepared and isolated, but it is preferable to prepare the complex in situ from ligand 1 or 2 and a metal pre-catalyst such as allylpalladium chloride dimer by simply mixing the two components in the desired solvent. The ligand to metal molar ratio may be in the range of about 0.5:1 to 5:1, preferably about 1:1 to 1.5:1. The amount of complex may vary between 0.00005 and 0.5 equivalents based on the reactant compound, with more complex usually providing faster reaction rates. The atmosphere is generally inert to the allylation reaction conditions. The allylation reaction can be run at atmospheric pressure or at slightly elevated pressure. The reaction is run at a temperature which affords a reasonable rate of conversion, which can be as low as −50° C. but is usually between ambient temperature and the boiling point (or apparent boiling point at elevated pressure) of the lowest boiling component of the reaction mixture. The reaction is usually run in the presence of a solvent chosen from aliphatic hydrocarbons such as hexane, heptane, octane and the like, aromatic hydrocarbons such as toluene, xylenes, and the like, cyclic or acyclic ethers such as tert-butyl methyl ether, diisopropyl ether, tetrahydrofuran and the like, halogenated aliphatic or aromatic hydrocarbons such as dichloromethane, tetrachloroethylene, chloroform, chlorobenzene and the like, or polar aprotic solvents such as dimethylformamide, dimethyl sulfoxide and the like. The reactions are optionally run in the presence of a proton acceptor such as an alkali salt of a carboxylic acid, an alkali carbonate, or an amine. The reactions are also often run in the presence of an acid scavenger such as N,O-bis (trimethylsilyl)trifluoroacetamide.

These reactions are exemplified by the asymmetric allylation reactions of various allylic electrophiles as shown below. The products generated from the asymmetric allylation reaction using a palladium complex formed in situ from ligands 1 or 2 are usually obtained in high enantiomeric excess (>80% ee).

Example 5

Dimethyl 2-(1,3-Diphenyl-2-propenyl)malonate (11a) Using Ligand 1a and Potassium Acetate in tert-Butyl Methyl Ether Ligand 1a (10.9 mg; 0.024 mmol; 0.024 equiv), allylpalladium chloride dimer (3.7 mg; 0.01 mmol; 0.01 equiv), and 1,3-diphenyl-2-propenyl acetate (10a; 259 mg; 1.03 mmol) were combined along with ca. 2 mg of potassium acetate. tert-Butyl methyl ether (TBME; 5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 15 h to afford >99% conversion to 11a, which had 94% ee according to chiral HPLC analysis. The volatiles were removed at reduced pressure and the crude product was flash-chromatographed and eluted with 1:9 ethyl acetate:heptane to afford 11a which was 99% pure by $^1$H NMR analysis (271 mg; 80% yield). Chiral HPLC (Chiralcel OD-H [Daicel], 250×4.6 mm, 98:2 hexane:isopropanol; 1 mL/min, λ=254 nm): 10a, $t_R$13.3, 14.5 min; 11a, $t_R$ 16.0, 16.9 min.

Example 6

Dimethyl 2-(1,3-Diphenyl-2-propenyl)malonate (11a) Using Ligand 1a and Potassium Acetate in Dichloromethane Ligand 1a (10.9 mg; 0.024 mmol; 0.024 equiv), allylpalladium chloride dimer (3.7 mg; 0.01 mmol; 0.01 equiv), and 1,3-diphenyl-2-propenyl acetate (10a; 252 mg; 1.00 mmol) were combined along with ca. 2 mg of potassium acetate. Dichloromethane (5 mL) was added and the reaction mixture was stirred at ambient temperature for 15 min. Dimethyl malonate (0.34 mL; 3.0 mmol; 3 equiv) and N,O-bis (trimethylsilyl)trifluoroacetamide (0.74 mL; 3.0 mmol; 3 equiv) were then added sequentially. The reaction mixture was stirred at ambient temperature for 20 h to afford 98.9% conversion to 11a, which had 95% ee according to chiral HPLC analysis.

Example 7

Dimethyl 2-(1,3-Diphenyl-2-propenyl)malonate (11a) Using Ligand 1a and Potassium Acetate in Toluene Ligand 1a (10.9 mg; 0.024 mmol; 0.024 equiv), allylpalladium chloride dimer (3.7 mg; 0.01 mmol; 0.01 equiv), and 1,3-diphenyl-2-propenyl acetate (10a; 252 mg; 1.00 mmol) were combined along with ca. 2 mg of potassium acetate. Toluene (5 mL) was added and the reaction mixture was stirred at ambient temperature for 15 min. Dimethyl malonate (0.34 mL; 3.0 mmol; 3 equiv) and N,O-bis (trimethylsilyl)trifluoroacetamide (0.74 mL; 3.0 mmol; 3 equiv) were then added sequentially. The reaction mixture was stirred at ambient temperature for 15 h to afford 11a which had 77% ee according to chiral HPLC analysis. The volatiles were removed at reduced pressure and the crude product was flash-chromatographed and eluted with 1:9 ethyl acetate:heptane to afford 11a which was 98.9% pure by $^1$H NMR analysis (271 mg; 80% yield).

Example 8

Dimethyl 2-(1,3-Diphenyl-2-propenyl)malonate (11a) Using Ligand 1a and Lithium Carbonate in tert-Butyl Methyl Ether Ligand 1a (10.9 mg; 0.024 mmol; 0.024 equiv), allylpalladium chloride dimer (3.7 mg; 0.01 mmol; 0.01 equiv), and 1,3-diphenyl-2-propenyl acetate (10a; 252 mg; 1.00 mmol) were combined along with ca. 2 mg of lithium carbonate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 15 h to afford >99% conversion to 11a, which had 96% ee according to chiral HPLC analysis.

Example 9

Dimethyl 2-(1,3-Diphenyl-2-propenyl)malonate (11a) Using Ligand 1a and Potassium Acetate in Tetrahydrofuran Ligand 1a (10.9 mg; 0.024 mmol; 0.024 equiv), allylpalladium chloride dimer (3.7 mg; 0.01 mmol; 0.01 equiv), and 1,3-diphenyl-2-propenyl acetate (10a; 252 mg; 1.00 mmol) were combined along with ca. 2 mg of potassium acetate. Tetrahydrofuran (THF; 5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 15 h to afford >99% conversion to 11a, which had 92% ee according to chiral HPLC analysis.

Example 10

Dimethyl 2-(1,3-Diphenyl-2-propenyl)malonate (11a) Using Ligand 1b and Lithium Carbonate in tert-Butyl Methyl Ether Ligand 1b (11.3 mg; 0.024 mmol; 0.019 equiv), allylpalladium chloride dimer (3.7 mg; 0.01 mmol; 0.008 equiv), and 1,3-diphenyl-2-propenyl acetate (10a; 313 mg; 1.28 mmol) were combined along with ca. 2 mg of lithium carbonate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred for 15 h at ambient temperature to afford >99% conversion to 11a, which had 99% ee according to chiral HPLC analysis. The volatiles were removed at reduced pressure and the crude product was flash-chromatographed and eluted with 1:9 ethyl acetate:heptane to afford 11a which was 98% pure by $^1$H NMR analysis (361 mg; 88% yield).

Example 11

Dimethyl 2-(1,3-Diphenyl-2-propenyl)malonate (11a) Using Ligand 1b and Lithium Carbonate in Toluene Ligand 1b (11.3 mg; 0.024 mmol; 0.024 equiv), allylpalladium chloride dimer (3.7 mg; 0.01 mmol; 0.01 equiv), and 1,3-diphenyl-2-propenyl acetate (10a; 252 mg; 1.00 mmol) were combined along with ca. 2 mg of lithium carbonate. Toluene (5 mL) was added and the reaction mixture was stirred at ambient temperature for 15 min. Dimethyl malonate (0.34 mL; 3.0 mmol; 3 equiv) and N,O-bis (trimethylsilyl)trifluoroacetamide (0.74 mL; 3.0 mmol; 3 equiv) were then added sequentially. The reaction mixture was stirred overnight at ambient temperature to afford >99% conversion to 11a, which had 94% ee according to chiral HPLC analysis. The volatiles were removed at reduced pressure and the crude product was flash-chromatographed and eluted with 1:9 ethyl acetate:heptane to afford 11a which was >99% pure by $^1$H NMR analysis (303 mg; 94% yield).

Exampple 12

Dimethyl 2-(1,3-Diphenyl-2-propenyl)malonate (11a) Using Ligand 1b and Lithium Carbonate in THF Ligand 1b (11.3 mg; 0.024 mmol; 0.024 equiv), allylpalladium chloride dimer (3.7 mg; 0.01 mmol; 0.01 equiv), and 1,3-diphenyl-2-propenyl acetate (10a; 252 mg; 1.00 mmol) were combined along with ca. 2 mg of lithium carbonate. Tetrahydrofuran (5 mL) was added and the reaction mixture was stirred at ambient temperature for 15 min. Dimethyl malonate (0.34 mL; 3.0 mmol; 3 equiv) and N,O-bis (trimethylsilyl)trifluoroacetamide (0.74 mL; 3.0 mmol; 3 equiv) were then added sequentially. The reaction mixture was stirred at ambient temperature for 15 h to afford >99% conversion to 11a, which had 97% ee according to chiral HPLC analysis. The volatiles were removed at reduced pressure and the crude product was flash-chromatographed and eluted with 1:9 ethyl acetate:heptane to afford 11a which was >99% pure by $^1$H NMR analysis (286 mg; 88% yield).

Example 13

Dimethyl 2-(1,3-Diphenyl-2-propenyl)malonate (11a) Using Ligand 1b and Lithium Carbonate in Dichloromethane Ligand 1b (11.3 mg; 0.024 mmol; 0.024 equiv), allylpalladium chloride dimer (3.7 mg; 0.01 mmol; 0.01 equiv), and 1,3-diphenyl-2-propenyl acetate (10a; 257 mg; 1.02 mmol) were combined along with ca. 2 mg of lithium carbonate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 15 h. The volatiles were removed at reduced pressure and the crude product was flash-chromatographed and eluted with 1:9 ethyl acetate:heptane to afford 11a which was 95% pure by $^1$H NMR analysis (247 mg; 71% yield) and possessed 98% ee according to chiral HPLC analysis.

Example 14

Dimethyl 2-(1,3-Diphenyl-2-propenyl)malonate (11a) Using Ligand 1b and Lithium Acetate in tert-Butyl Methyl Ether Ligand 1b (11.3 mg; 0.024 mmol; 0.024 equiv), allylpalladium chloride dimer (3.7 mg; 0.01 mmol; 0.01 equiv), and 1,3-diphenyl-2-propenyl acetate (10a; 260 mg; 1.03 mmol) were combined along with ca. 2 mg of lithium acetate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 15 h to afford >99% conversion to 11a, which had 73% ee according to chiral HPLC analysis. The volatiles were removed at reduced pressure and the crude product was flash-chromatographed and eluted with 1:9 ethyl acetate:heptane to afford 11a which was 94% pure by $^1$H NMR analysis (310 mg; 87% yield).

Example 15

Dimethyl 2-(1,3-Diphenyl-2-propenyl)malonate (11a) Using Ligand 1b and Sodium Acetate in tert-Butyl Methyl Ether Ligand 1b (11.3 mg; 0.024 mmol; 0.024 equiv), allylpalladium chloride dimer (3.7 mg; 0.01 mmol; 0.01 equiv), and 1,3-diphenyl-2-propenyl acetate (10a; 255 mg; 1.01 mmol) were combined along with ca. 2 mg of lithium carbonate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 15 h to afford 91% conversion to 11a, which had 96% ee according to chiral HPLC analysis. The volatiles were removed at reduced pressure and the crude product was flash-chromatographed and eluted with 1:9 ethyl acetate:heptane to afford 11a which was 94% pure by $^1$H NMR analysis (301 mg; 86% yield).

Example 16

Dimethyl 2-(1,3-Diphenyl-2-propenyl)malonate (11a) Using Ligand 1b and Lithium Carbonate in tert-Butyl Methyl Ether Ligand 1b (11.3 mg; 0.024 mmol; 0.024 equiv), allylpalladium chloride dimer (3.7 mg; 0.01 mmol; 0.01 equiv), and 1,3-diphenyl-2-propenyl acetate (10a; 252 mg; 1.00 mmol) were combined along with ca. 2 mg of lithium carbonate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 15 h to afford 99% conversion to 11a, which had 98% ee according to chiral HPLC analysis. The volatiles were removed at reduced pressure and the crude product was flash-chromatographed and eluted with 1:9 ethyl acetate:heptane to afford 11a which was 99% pure by $^1$H NMR analysis (298 mg; 91% yield).

Example 17

Dimethyl 2-(1,3-Diphenyl-2-propenyl)malonate (11a) Using Ligand 1b and Sodium Carbonate in tert-Butyl Methyl Ether Ligand 1b (11.3 mg; 0.024 mmol; 0.023 equiv), allylpalladium chloride dimer (3.7 mg; 0.01 mmol; 0.009 equiv), and 1,3-diphenyl-2-propenyl acetate (10a; 268 mg; 1.06 mmol) were combined along with ca. 2 mg of sodium carbonate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 40 h to afford >99% conversion to 11a, which had 97% ee according to chiral HPLC analysis. The volatiles were removed at reduced pressure and the crude product was flash-chromatographed and eluted with 1:9 ethyl acetate:heptane to afford 11a which was 97% pure by $^1$H NMR analysis (300 mg; 84% yield).

Example 18

Dimethyl 2-(1,3-Diphenyl-2-propenyl)malonate (11a) Using Ligand 1b and Potassium Carbonate in tert-Butyl Methyl Ether Ligand 1b (11.3 mg; 0.024 mmol; 0.024 equiv), allylpalladium chloride dimer (3.7 mg; 0.01 mmol; 0.01 equiv); and 1,3-diphenyl-2-propenyl acetate (10a; 256 mg; 1.01 mmol) were combined along with ca. 2 mg of potassium carbonate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 40 h to afford >99% conversion to 11a, which had 96% ee according to chiral HPLC analysis. The volatiles were removed at reduced pressure and the crude product was flash-chromatographed and eluted with 1:9 ethyl acetate:heptane to afford 11a which was 99% pure by $^1$H NMR analysis (271 mg; 81% yield).

Example 19

Dimethyl 2-(1,3-Diphenyl-2-propenyl)malonate (11a) Using Ligand 1c and Potassium Acetate in Dichloromethane Ligand 1c (12.4 mg; 0.024 mmol; 0.024 equiv), allylpalladium chloride dimer (3.7 mg; 0.01 mmol; 0.01 equiv), and 1,3-diphenyl-2-propenyl acetate (10a; 252 mg; 1.00 mmol) were combined along with ca. 2 mg of potassium acetate. Dichloromethane (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 38 h to afford 30% conversion to 11a, which had 42% ee according to chiral HPLC analysis.

Example 20

Dimethyl 2-(1,3-Diphenyl-2-propenyl)malonate (11a) Using Ligand 1c and Potassium Acetate in tert-Butyl Methyl Ether Ligand 1c (12.4 mg; 0.024 mmol; 0.024 equiv), allylpalladium chloride dimer (3.7 mg; 0.01 mmol; 0.01 equiv), and 1,3-diphenyl-2-propenyl acetate (10a; 252 mg; 1.00 mmol) were combined along with ca. 2 mg of potassium acetate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 38 h to afford 27% conversion to 11a, which had 25% ee according to chiral HPLC analysis.

Example 21

Dimethyl 2-(2-Cyclohexenyl)malonate(11b) Using Ligand 1a and Lithium Carbonate in tert-Butyl Methyl Ether Ligand 1a (10.9 mg; 0.024 mmol; 0.024 equiv), allylpalladium chloride dimer (3.7 mg; 0.01 mmol; 0.01 equiv), and 2-cyclohexenyl acetate (10b; 140 mg; 1.00 mmol) were combined along with ca. 2 mg of lithium carbonate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 6 days to afford 93% conversion to 11b, which had 83% ee according to chiral GC analysis.

Example 22

Dimethyl 2-(2-Cyclohexenyl)malonate(11b) Using Ligand 1b and Lithium Carbonate in tert-Butyl Methyl Ether Ligand 1b (11.3 mg; 0.024 mmol; 0.024 equiv), allylpalladium chloride dimer (3.7 mg; 0.01 mmol; 0.01 equiv), and 2-cyclohexenyl acetate (10b; 140 mg; 1.00 mmol) were combined along with ca. 2 mg of lithium carbonate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 6 days to afford 56% conversion to 11b, which had 83% ee according to chiral GC analysis.

Example 23

Dimethyl 2-(2-Cyclohexenyl)malonate(11b) Using Ligand 1b and Potassium Acetate in tert-Butyl Methyl Ether Ligand 1b (11.3 mg; 0.024 mmol; 0.024 equiv), allylpalladium chloride dimer (3.7 mg; 0.01 mmol; 0.01 equiv), and 2-cyclohexenyl acetate (10b; 140 mg; 1.00 mmol) were combined along with ca. 2 mg of potassium acetate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 6 days to afford 14% conversion to 11b, which had 76% ee according to chiral GC analysis.

Example 24

Dimethyl 2-(2-Cyclohexenyl)malonate(11b) Using Ligand 1c and Lithium Carbonate in tert-Butyl Methyl Ether Ligand 1c (12.4 mg; 0.024 mmol; 0.024 equiv), allylpalladium chloride dimer (3.7 mg; 0.01 mmol; 0.01 equiv), and 2-cyclohexenyl acetate (10b; 140 mg; 1.00 mmol) were combined along with ca. 2 mg of lithium carbonate. tert-Butyl methyl ether (5 mL) was added and the reaction mixture was stirred at ambient temperature for 15 min. Dimethyl malonate (0.34 mL; 3.0 mmol; 3 equiv) and N,O-bis(trimethylsilyl)trifluoroacetamide (0.74 mL; 3.0 mmol; 3 equiv) were then added sequentially. The reaction mixture was stirred at ambient temperature for 6 days to afford 70% conversion to 11b, which had 73% ee according to chiral GC analysis.

The invention has been described in detail with particular reference to preferred embodiments thereof, but it will be understood that variations and modifications can be effected within the spirit and scope of the invention.

I claim:

1. A substantially enantiomerically pure phosphine-amide having formula 1:

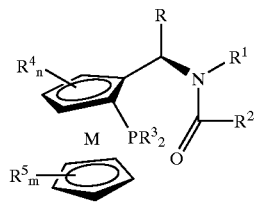

wherein
R is selected from substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

$R^1$, $R^2$, $R^3$, $R^4$, and $R^5$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

n is 0 to 3;

m is 0 to 5; and

M is selected from the metals of Groups IVB, VB, VIB, VIIB and VIII.

2. A compound according to claim 1 wherein R is methyl, $R^2$ is methyl, ethyl, or phenyl, $R^3$ is phenyl, n and m are 0, and M is iron, ruthenium, or osmium.

3. A compound according to claim 2 where $R^1$ is hydrogen and M is iron.

4. A substantially enantiomerically pure phosphine-amide having formula 2:

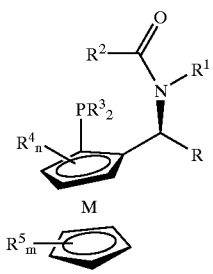

2 wherein

R is selected from substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

$R^1$, $R^2$, $R^3$, $R^4$, and $R^5$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

n is 0 to 3;

m is 0 to 5; and

M is selected from the metals of Groups IVB, VB, VIB, VIIB and VIII.

5. A compound according to claim 4 where R is methyl, $R^2$ is methyl, ethyl, or phenyl, $R^3$ is phenyl, n and m are 0, and M is iron, ruthenium, or osmium.

6. A compound according to claim 5 where $R^1$ is hydrogen and M is iron.

7. A composition comprising a substantially enantiomerically pure compound defined in claim 1 in complex association with a Group VIb or a Group VIII metal.

8. A composition according to claim 7 wherein (i) in the substantially enantiomerically pure compound defined in claim 1 R is methyl, $R^1$ is hydrogen, $R^2$ is methyl, ethyl, or phenyl, $R^3$ is phenyl, n and m are 0, and M is iron, ruthenium, or osmium and (ii) the Group VIb or Group VIII metal is palladium.

9. A composition comprising a substantially enantiomerically pure compound defined in claim 4 in complex association with a Group VIb or a Group VIII metal.

10. A composition according to claim 9 wherein (i) in the substantially enantiomerically pure compound defined in claim 4 R is methyl, $R^1$ is hydrogen, $R^2$ is methyl, ethyl, or phenyl, $R^3$ is phenyl, n and m are 0, and M is iron, ruthenium, or osmium and (ii) the Group VIb or Group VIII metal is palladium.

11. A process for preparing a substantially enantiomerically pure compound having formula 1:

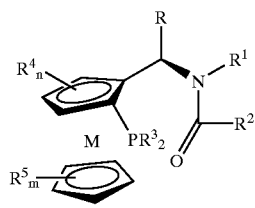

1 which comprises the steps of:

(1) contacting an amine having formula 3:

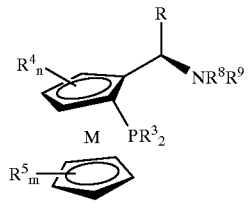

3 with a carboxylic anhydride having the formula $(R^{10}CO)_2O$ to obtain an ester compound having formula 4:

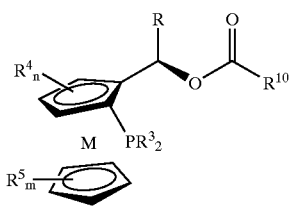

4

(2) contacting the ester 4 with an amine having the formula $H_2N$—$R^1$ to obtain an intermediate compound having formula 5:

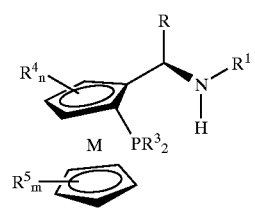

5

(3) contacting intermediate compound 5 with an acid anhydride or acid chloride of formula $(R^2CO)_2O$ or $R^2COX$;

wherein

R, $R^8$, and $R^9$ are independently selected from substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted or unsubstituted $C_4$–$C_{20}$ heteroaryl wherein the heteroatoms are selected from sulfur, nitrogen, and oxygen;

$R^1$, $R^2$, $R^3$, $R^4$, and $R^5$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

n is 0 to 3;

m is 0 to 5;

M is selected from the metals of Groups IVB, VB, VIB, VIIB and VIII;

$R^{10}$ is a $C_1$ to $C_4$ alkyl radical; and

X is a halide, a sulfonate, an imidazole or hydrogen.

12. A process according to claim 11 wherein R, $R^8$, and $R^9$ are methyl, $R^2$ is methyl, ethyl, or phenyl, $R^3$ is phenyl, X is chlorine or bromine, n and m are 0, and M is iron, ruthenium, or osmium.

13. A process according to claim 12 where $R^1$ is hydrogen, X is chlorine, and M is iron.

14. A process according to claim 11 wherein the carboxylic anhydride of formula $(R^{10}CO)_2O$ is selected from acetic, propionic, or butyric anhydride, the carboxylic anhydride of formula $(R^2CO)_2O$ is acetic anhydride or propionic anhydride or the acid halide of formula $R^2COX$ is benzoyl chloride, and step (2) is conducted in the presence of a lower alcohol solvent selected from methanol, ethanol, n-propanol, isopropanol, n-butanol, sec-butanol, or tert-butanol.

15. A process according to claim 14 wherein step (3) is carried out in the presence of a $C_3$–$C_{15}$ trialkylamine and a non-polar, aprotic solvent selected from aliphatic and aromatic hydrocarbons containing 6 to 10 carbon atoms, halogenated hydrocarbons containing up to about 6 carbon atoms, and cyclic and acyclic ethers containing from about 4 to 8 carbon atoms.

16. A process according to claim 15 wherein step (3) is carried out in the presence of triethylamine and toluene.

17. A process for preparing a substantially enantiomerically pure compound having formula 2:

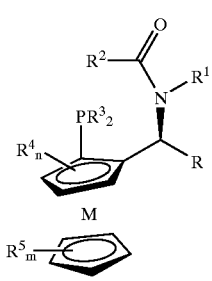

2 which comprises the steps of:

(1) contacting an amine having formula 6:

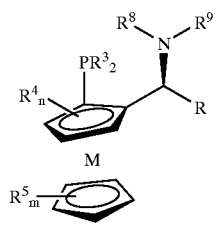

6 with a carboxylic anhydride having the formula $(R^{10}CO)_2O$ to obtain an ester compound having formula 7:

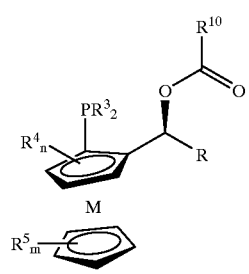

7

(2) contacting the ester 4 with an amine having the formula $H_2N$—$R^1$ to obtain an intermediate compound having formula 8:

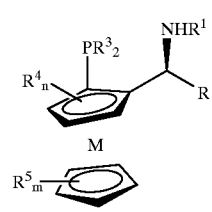

8

(3) contacting intermediate compound 5 with an acid anhydride or acid chloride of formula $(R^2CO)_2O$ or $R^2COX$;

wherein

R, $R^8$, and $R^9$ are independently selected from substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

$R^1$, $R^2$, $R^3$, $R^4$, and $R^5$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

n is 0 to 3;

m is 0 to 5;

M is selected from the metals of Groups IVB, VB, VIB, VIIB and VIII;

$R^{10}$ is a $C_1$ to $C_4$ alkyl radical; and

X is a halide, a sulfonate, an imidazole or hydrogen.

18. A process according to claim 17 wherein R, $R^8$, and $R^9$ are methyl, $R^2$ is methyl, ethyl, or phenyl, $R^3$ is phenyl, X is chlorine or bromine, n and m are 0, and M is iron, ruthenium, or osmium.

19. A process according to claim 18 where $R^1$ is hydrogen, X is chlorine, and M is iron.

20. A process according to claim 17 wherein the carboxylic anhydride of formula $(R^{10}CO)_2O$ is selected from acetic, propionic, or butyric anhydride, the carboxylic anhydride of formula $(R^2CO)_2O$ is acetic anhydride or propionic anhydride or the acid halide of formula $R^2COX$ is benzoyl chloride, and step (2) is conducted in the presence of a lower alcohol solvent selected from methanol, ethanol, n-propanol, isopropanol, n-butanol, sec-butanol, or tert-butanol.

21. A process according to claim 20 wherein step (3) is carried out in the presence of a $C_3$–$C_{15}$ trialkylamine and a non-polar, aprotic solvent selected from aliphatic and aromatic hydrocarbons containing 6 to 10 carbon atoms, halogenated hydrocarbons containing up to about 6 carbon atoms, and cyclic and acyclic ethers containing from about 4 to 8 carbon atoms.

22. A process according to claim 21 wherein step (3) is carried out in the presence of triethylamine and toluene.

23. A method for asymmetrically allylating an allylic electrophile which comprises contacting the allylic electrophile with a nucleophile in the presence of a catalyst complex defined in any of claims 7 through 10.

24. A method according to claim 23 wherein the allylic electrophile compound has formula 10:

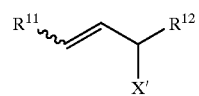

wherein:
$R^{11}$ and $R^{12}$ are independently selected from hydrogen, substituted and unsubstituted, branched- and straight-chain $C_1$ to $C_{20}$ alkyl, substituted and unsubstituted $C_3$ to $C_8$ cycloalkyl, substituted and unsubstituted $C_6$ to $C_{20}$ carbocyclic aryl, and substituted and unsubstituted $C_4$ to $C_{20}$ heteroaryl wherein the heteroatoms are selected from sulfur, nitrogen, or oxygen; or
$R^{11}$ and $R^{12}$ collectively represent a substituted or unsubstituted alkylene group of 0–5 chain carbon atoms; and
X' is chosen from chloride, bromide, iodide, sulfonates of formula $OSOR^{13}$, esters of formula —$OCOR^{13}$, and carbonates of formula —$OCOOR^{13}$, wherein $R^{13}$ is selected from hydrogen, substituted and unsubstituted, branched- and straight-chain $C_1$ to $C_{20}$ alkyl, substituted and unsubstituted $C_3$ to $C_8$ cycloalkyl, substituted and unsubstituted $C_6$ to $C_{20}$ carbocyclic aryl, and substituted and unsubstituted $C_4$ to $C_{20}$ heteroaryl wherein the heteroatoms are selected from sulfur, nitrogen, or oxygen.

25. A method according to claim 23 wherein the nucleophile is a soft carbon acid, substituted or unsubstituted $C_1$–$C_{20}$ alcohols, substituted or unsubstituted phenols, and substituted or unsubstituted $C_1$–$C_{20}$ amines.

26. A method according to claim 25 wherein the soft carbon acid is a malonate, a 3-ketoester or a 2-cyanoester.

* * * * *

UNITED STATES PATENT AND TRADEMARK OFFICE
CERTIFICATE OF CORRECTION

PATENT NO. : 6,620,954 B1
DATED : September 16, 2003
INVENTOR(S) : Boaz

It is certified that error appears in the above-identified patent and that said Letters Patent is hereby corrected as shown below:

<u>Column 22,</u>
Line 18, "$OSOR^{13}$" should be -- $OSO2R^{13}$ --.

Signed and Sealed this

Eleventh Day of November, 2003

JAMES E. ROGAN
*Director of the United States Patent and Trademark Office*